US010251843B2

(12) United States Patent
Gao et al.

(10) Patent No.: US 10,251,843 B2
(45) Date of Patent: *Apr. 9, 2019

(54) CROSSLINKED NANOPARTICLE COMPOSITION

(71) Applicant: San Heh Pharmaceutical Corporation, Kaohsiung (TW)

(72) Inventors: Weiwei Gao, La Jolla, CA (US); Yu-Chen Chen, La Jolla, CA (US)

(73) Assignee: SAN HEH PHARMACEUTICAL CORPORATION, Kaohsiung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,768

(22) Filed: Jul. 14, 2017

(65) Prior Publication Data

US 2017/0319507 A1    Nov. 9, 2017

Related U.S. Application Data

(63) Continuation of application No. 14/630,372, filed on Feb. 24, 2015, now Pat. No. 9,724,307.

(51) Int. Cl.
*A61K 9/51* (2006.01)
*A61K 31/43* (2006.01)
*A61K 9/107* (2006.01)

(52) U.S. Cl.
CPC .......... *A61K 9/5192* (2013.01); *A61K 9/1075* (2013.01); *A61K 9/5123* (2013.01); *A61K 9/5161* (2013.01); *A61K 31/43* (2013.01); *Y02A 50/473* (2018.01); *Y02A 50/481* (2018.01); *Y10S 977/773* (2013.01); *Y10S 977/896* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 5,863,461 A | 1/1999 | Ansmann et al. | |
| 6,610,328 B2 | 8/2003 | Rudnic et al. | |
| 7,309,500 B2 | 12/2007 | Kim et al. | |
| 7,883,723 B2 | 2/2011 | Nah et al. | |
| 8,354,094 B1 | 1/2013 | Sung et al. | |
| 9,724,307 B2 * | 8/2017 | Gao ................... | A61K 9/5192 |
| 2003/0082148 A1 | 5/2003 | Ludwig et al. | |
| 2003/0161886 A1 | 8/2003 | Dickinson et al. | |
| 2006/0216353 A1 | 9/2006 | Liversidge et al. | |
| 2007/0264199 A1 | 11/2007 | Labhasetwar et al. | |
| 2009/0221764 A1 | 9/2009 | Shumaker-parry et al. | |
| 2010/0015232 A1 | 1/2010 | Besenbacher et al. | |
| 2010/0310639 A1 | 12/2010 | Metcalfe | |
| 2011/0059162 A1 | 3/2011 | Madrigal-carballo et al. | |
| 2011/0158901 A1 | 6/2011 | Santra | |

FOREIGN PATENT DOCUMENTS

CN     101766820 A  *  7/2010

OTHER PUBLICATIONS

English Translation of CN 101766820 A. Obtained from Google Patents on Aug. 2, 2018 at https://patents.google.com/patent/CN101766820A/en?oq=CN101766820A. Originally published in Chinese on Jul. 7, 2010. 5 printed pages. (Year: 2010).*
Da Kumar, S Dharmendra, M Jhansee, N Shrikant, SP Pandey. "Development and Characterization of Chitosan Nanoparticles Loaded with Amoxycillin." International Research Journal of Pharmacy, vol. 2(5), 2011, pp. 145-151. (Year: 2011).*
JK Patel, MM Patel. "Stomach Specific Anti-Helicobacter Pylori Therapy: Preparation and Evaluation of Amoxicillin-Loaded Chitosan Mucoadhesive Microspheres." Current Drug Delivery, vol. 4, 2007, pp. 41-50. (Year: 2007).*
S Arora, RD Budhiraja. Chitosan-alginate microcapsules of amoxicillin for gastric stability and mucoadhesion. Journal of Advanced Pharmaceutical Technology & Research, vol. 3 Issue 1, Jan.-Mar. 2012, pp. 68-74. (Year: 2012).*
Abstract of J Balcerzak, M Kucharska, B Gruchala. "Preparation of Micro and Nanostructures of Chitosan by Ultrasonic Coalescence of W/O Emulsions." Progress in Chemistry and Application of Chitin and its Derivatives. vol. 18, 2013, abstract is 1 printed page.
Agnihotri et al. Recent advances on chitosan-based micro-and nanoparticles in drug delivery. Journal of Controlled Release 100 (2004) 5-28.
Arora, et al.; "Amoxicillin Loaded Chitosan-Alginate Polyelectrolyte Complex Nanoparticles as Mucopenetrating Delivery System for H. Pylori"; Sci. Pharm.; vol. 79, No. 3, pp. 673-694 (Sep. 2011).
Arora, et al.; "Chitosan-Alginate Microcapsules of Amoxicillin for Gastric Stability and Mucoadhesion"; Journal of Advanced Pharmaceutical Technology and Research; vol. 3, No. 1, pp. 68-74 (Jan. 2012).
D Kowalczyk, M Kordowska-Wiater, J Nowak, B Baraniak. "Characterization of films based on chitosan lactate and its blends with oxidized starch and gelatin." International Journal of Biological Macromolecules, vol. 77, 2015, pp. 350-359.
DA Kumar, S Dharmendra, M Jhansee, N. Shrikant P Shiv P. "Development and Characterization of Chitosan Nanoparticles Loaded with Amoxycillin." International Research Journal of Pharmacy, ISSN 2230-8407, vol. 2(5), 2011, pp. 145-151, 6 printed pages.

(Continued)

Primary Examiner — Isaac Shomer
(74) Attorney, Agent, or Firm — Perkins Coie LLP; Viola T. Kung (57) ABSTRACT

The present invention provides a process for preparing the nanoparticles. The process comprises first forming a water-in-oil emulsion from chitosan lactate, amoxicillin, dioctyl sodium sulfosuccinate, glutaraldehyde or bis[sulfosuccinimidyl] suberate, and oil, and sonicating the mixture of to form nanoparticles comprising chitosan crosslinked by dioctyl sodium sulfosuccinate and glutaraldehyde or by dioctyl sodium sulfosuccinate and bis[sulfosuccinimidyl] suberate, wherein the nanoparticles have an average diameter of 100-600 nm and have amoxicillin entrapped by the crosslinked chitosan. The present invention is also directed to nanoparticles comprising crosslinked chitosan and amoxicillin, wherein amoxicillin is entrapped by the crosslinked chitosan. The nanoparticles have an average diameter of 100-600 nm, and the entrapped amoxicillin is at least 5% (w/w) of the total weight nanoparticles.

12 Claims, 3 Drawing Sheets

(56) References Cited

OTHER PUBLICATIONS

Dev, Ashish et al., "Preparation of poly(lactic acid)/chitosan nanoparticles for anti-HIV drug delivery applications", Carbohydrate Polymers 80, Jan. 7, 2010, pp. 833-838.

E Onuigbo, A Onugwu, M Nwocha, A Odiase, A Attama. "Preparation and in vitro evaluation of amoxicillin encapsulated in alginate-coated chitosan microparticles." Tropical Journal of Pharmaceutical Research, vol. 15(11), Nov. 2016, pp. 2303-2309.

Giri et al. Modified chitosan hydrogels as drug delivery and tissue engineering systems:present status and applications. Acta Pharmaceutica Sinica B 2012; 2(5):439-449.

J Balcerzak, M Kucharska, B Gruchala. "Preparation of Micro and Nanostructures of Chitosan by Ultrasonic Coalescence of W/O Emulsions." Progress in Chemistry and Application of Chitin and its Derivatives. vol. 18, 2013, pp. 13-20.

JK Patel, MM Patel. "Stomach Specific Anti-Helicobacter Pylori Therapy: Preparation and Evaluation of Amoxicillin-Loaded Chitosan Mucoadhesive Microspheres." Current Drug Delivery, vol. 4, 2007, pp. 41-50.

Kumar, et al.; "Development and Characterization of Chitosan Nanoparticles Loaded With Amoxycillin"; International Research Journal of Pharmacy; vol. 2, No. 5, pp. 145-151 (Jul. 5, 2011).

Lin, et al.; "Genipin-Cross-Linked Fucose-Chitosan/Heparin Nanoparticles for the Eradication of Helicobater Pylori"; Biomaterials; vol. 34, No. 18, pp. 4466-4479 (2013).

Mirzaei, et al.; "Studies on Glutaraldehyde Crosslinked Chitosan Hydrogel Properties for Drug Delivery Systems"; International Journal of Polymeric Materials and Polymeric Biomaterials; vol. 62, pp. 605-611 ((Dec. 26, 2012).

Mitra et al. Chitosan Microsheres in Novel Drug Delivefy Systems. Indian J Pharm Sci. 2011 73(4):355-366.

Non-Final Office Action dated Dec. 4, 2014, U.S. Appl. No. 14/481,826.

Patel, et al.; "Stomach Specific Anti-Helicobacter Pylori Therapy: Preparation and Evaluation of Amoxicillin-Loaded Chitosan Mucoadhesive Microspheres"; Ctirrent Drug Delivery; vol. 4, pp. 41-50 (2007).

Ramachandran, et al.; "Formulation and Characterization of Glutaraldehyde Cross-Linked Chitosan Biodegradable Microspheres Loaded with Famotidine"; Tropical Journal of Pharmaceutical Research; vol. 10, No. 3, pp. 309-316 (Jun. 2011).

Ramteke, et al.; "Amoxicillin, Clarithromycin, and Omeprazole Based Targeted Nanoparttcles for the Treatment of H. Pylori"; Journal of Drug Targeting; vol. 17, No. 3, pp. 225-234 (2009).

Ravel, et al.; "Formulation and In Vitro Characterization of Spray Dried Microspheres of Amoxicillin", Acta Pharma; vol. 60, pp. 455-465 (2010).

S Arora, RD Budhiraja. "Chitosan-alginate Microcapsules of Amoxicillin for Gastric Stability and Mucoadhesion." Journal of Advanced Pharmaceutical Technology and Research. vol. 3 Issue 1, Jan.-Mar. 2012, pp. 68-74.

SM Berge, LD Bighley, DC Monkhouse. "Pharmaceutical Salts." Journal of Pharmaceutical Sciences, vol. 66 No. 1, Jan. 1977, pp. 1-19.

Anal et al. "Ionotropic cross-linked chitosan microspheres for controlled release of ampicillin", International Journal of Pharmaceutics vol. 312, Feb. 23, 2006, pp. 166-173.

\* cited by examiner

CROSSLINKED NANOPARTICLE COMPOSITION

This application is a continuation of U.S. application Ser. No. 14/630,372, filed Feb. 24, 2015, which is incorporated herein by reference in its entirety.

FIELD OF THE INVENTION

The present invention relates to a process for preparing nanoparticles of 100-600 nm in size by first forming a water-in-oil emulsion from chitosan lactate, amoxicillin, dioctyl sodium sulfosuccinate, glutaraldehyde or bis[sulfosuccinimidyl] suberate, and oil, and then sonicating the mixture of to form nanoparticles.

BACKGROUND OF THE INVENTION

Amoxicillin is a semi-synthetic, orally absorbed, broad-spectrum antibiotic. Chemically, it is (2S,5R,6R)-6-[(R)-(−)-2-amino-2-(p-hydroxyphenyl)acetamido]-3,3-dimethyl-7-oxo-4-thia-1-azabicyclo[3.2.0]heptane-2-carboxylic acid trihydrate. Amoxicillin is widely used in the standard eradication treatment of gastric and duodenal ulcers, which are associated with *Helicobacter pylori* infection, combined with a second antibiotic and an acid-suppressing agent. *H. pylori,* a prevalent human-specific pathogen, is a causative agent in chronic active gastritis, gastric and duodenal ulcers, and gastric adenocarcinoma. Treatment of *H. pylori* remains a challenging proposition. One reason for incomplete eradication of *H. pylori* may be the short residence time of the dosage form in the stomach so that effective antimicrobial concentration cannot be achieved in the gastric mucous layer or epithelial cell surfaces where *H. pylori* exists. Another reason may be the degradation of amoxicillin in gastric acid. A number of researchers have prepared and reported new amoxicillin formulations such as float tablets, mucoadhesive tablets, and formulations with pH-sensitive excipients, which are able to reside in the gastrointestinal tract for a longer extended period of time for more effective *H. pylori* eradication.

There is a need for an amoxicillin composition for delivering amoxicillin in the stomach, which would provide a long resident time and sustained action, and increase the efficiency of the drug.

BRIEF DESCRIPTION OF THE DRAWING

FIG. 1 depicts the features of the nanoparticles of the present invention for oral delivery of amoxicillin FIG. 2 shows the characterization of nanoparticles. (A) shows that the particles have an average hydrodynamic diameter of 324.6 nm and a PDI of 0.2. (B) shows that under the SEM, the dry powder has a particulate morphology with an average diameter of about 300 nm.

FIG. 3 shows the amoxicillin loading yield in the nanoparticle formulation at various initial drug input concentrations.

FIG. 4 shows the release profiles of amoxicillin in the nanoparticle formulation at pH=2.0, 5.0, 6.0, and 7.4.

FIG. 5 shows in vivo pharmacokinetic profiles of amoxicillin in a free drug form and in a nanoparticle formulation dosed orally in a mouse model (n=10 for each group). Insert shows the pharmacokinetic profiles between 0 to 5 hours.

FIG. 6 shows the antimicrobial activity of amoxicillin in the nanoparticle formulation and in free drug form against *H. pylori* bacteria. (A) shows the determination of the minimum inhibitory concentration (MIC) value. (B) shows the determination of the minimum bactericidal concentration (MBC) value.

DETAILED DESCRIPTION OF THE INVENTION

Definition

"About" is defined as ±10% of the recited value.

"Chitosan" is defined as deacetylated chitin, or poly(D-gluscosamine). It is a linear polysaccharide composed of randomly distributed β-(1-4)-linked D-glucosamine (deacetylated unit) and N-acetyl-D-glucosamine (acetylated unit). Preferred chitosan for the present invention is at least 60%, or 70%, or 80%, 85%, or 90% deacetylated. For example, chitosan can be obtained in molecular weight of about 110,000-150,000 daltons, 60,000-120,000 daltons, or 40,000-60,000 daltons. Chitosan in general has the structure as shown below.

Chitosan lactate is a lactate salt of chitosan. It is also named Chitosan 2-hydroxypropanoate, chitosan oligosaccharide lactate", and it has an average molecular weight of 4,000-6,000, or 5,000 daltons. Chitosan Lactate is white or light yellow solid powder, soluble in water and insoluble in organic solvent such as alcohol. Its liquid is colorless or light yellow cleared solution with stable property.

"Drug loading yield" of nanoparticles is defined as the ratio (%) of the weight of the entrapped drug to the total weight of the drug-loaded nanoparticles including both excipients and drug.

"Nanoparticles" are defined as particles with a diameter below 1 μm and between 1-999 nanometer.

The inventors have discovered a nanoparticle composition comprising crosslinked chitosan and amoxicillin, where amoxicillin is entrapped by a nanoparticle matrix of the crosslinked chitosan. The nanoparticle composition of the present invention protects amoxicillin from degradation, increases drug residence time at the target site, increases drug retention time after oral administration, and thus improves bioavailability and efficacy of amoxicillin.

Nanoparticles for oral delivery of amoxicillin have advantages over free amoxicillin or larger size microspheres of diameters greater than 1 μm. Due to the small size and relative mobility, nanoparticles are capable to penetrate throughout the submucosal layers in GI tract, while microspheres of micron size predominantly localized in the epithelial lining. As the result of the penetration, nanoparticles can be easily trapped and retained at the mucosal layer, which increases the residence time at the site of absorption and provides extended and controlled release of amoxicillin. In addition, nanoparticles, when compared to bigger particles, have a larger surface-to-volume ratio. When chitosan is formulated into nanoparticles, it exposes a higher surface area for mucosal adhesion, further increasing drug absorption for efficient amoxicillin delivery.

Chitosan possesses some ideal properties of polymeric carriers for nanoparticles such as mucoadhesive, biocompatible, biodegradable, nontoxic, and inexpensive. Furthermore, it possesses positively charge and exhibits absorption enhancing effect. Chitosan has a lower bulk density (<0.6 g/cm$^3$) than gastric fluid. By combining chitosan-based polymer system with a unique formulation process, nanoparticles of the present invention are capable of maintaining negative buoyancy and floating upward in the stomach, thereby increasing nanoparticle retention after oral administration. A floating nanoparticle formulation confer a range of advantages for drug delivery, including enhanced drug bioavailability, reduced dosing frequency, and targeted therapy for local ailments in the upper GI tract.

In the present composition, drug encapsulation is achieved through the cross-linking of chitosan. The formulation process is optimized so that the chitosan polymer backbone is largely intact after the cross-linking and the unique mucosal adhesive property of chitosan is preserved. The primary component of the nanoparticle composition is chitosan, which allows the particle to engage mucoadhesive interactions with mucin in the lining of GI tract. These interactions are complex with contributions from electrostatic attraction, hydrogen bonding, and hydrophobic effects. Adhesive characteristics allow nanoparticles to actively bind to the mucosal layer of the stomach and the GI tract below, thereby increasing nanoparticle retention in vivo.

Figure 1:
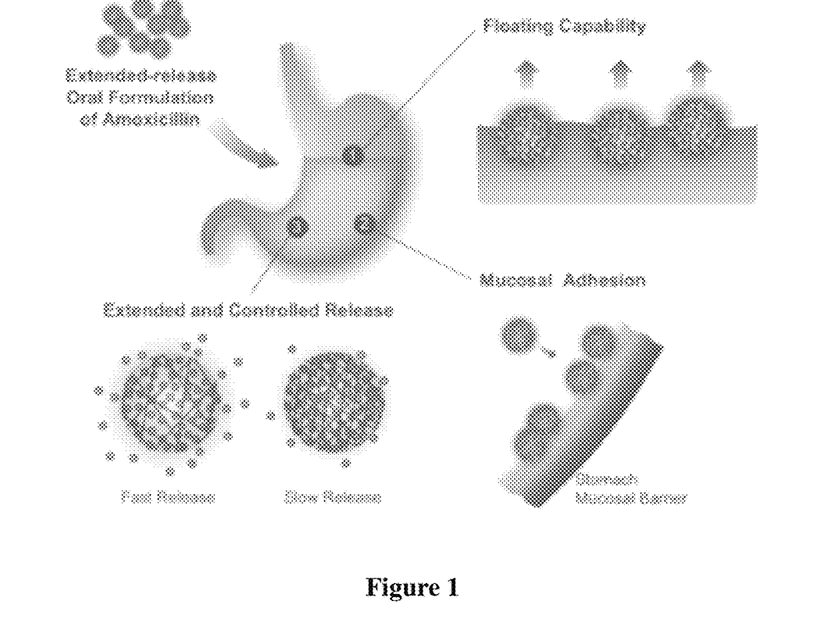

The features of the nanoparticles of the present invention for oral delivery of amoxicillin is shown is FIG. 1.

Nanoparticle Composition

The present invention is directed to nanoparticles comprising crosslinked chitosan and amoxicillin, wherein chitosan is crosslinked by dioctyl sodium sulfosuccinate and glutaraldehyde or by dioctyl sodium sulfosuccinate and bis[sulfosuccinimidyl] suberate, and amoxicillin is entrapped by the crosslinked chitosan.

"Entrapped" as used herein, refers to amoxicillin is encapsulated by, or attached to, or bound to, the crosslinked chitosan. In the nanoparticles, the crosslinked chitosan is the main polymer (over 50% w/w of the nanoparticles) that forms the matrix of the nanoparticles. In one embodiment, a small amount of other polymers (less than 40%, preferably less than 30%, 20%, or 10%) can be added to the nanoparticle matrix. In another embodiment, the nanoparticles of the present invention does not contain a substantial amount of any "other polymer" than crosslinked chitosan; i.e., the nanoparticles contains less than 10%, 5%, or 2%, or 1%, or 0.1%, or 0% (w/w) of any other polymer. "Other polymers" include, but not limited to, alginate, heparin, poly(acrylic acid), tannin, Carbopol®, fucose, copolymer of acrylamide, acrylic acid, and methacrylate.

The nanoparticles of the present invention have an average diameter of about 50-900 nm; preferably have an average diameter of about 100-600 nm, or 250-400 nm. At least 80%, preferably 85%, 90%, or 95% of the particles in the nanoparticle composition have a size less than 1 micron.

In one embodiment, the nanoparticles have an average diameter of about 100-600 nm, and the particle size distribution is that at least 80% of the nanoparticles have a diameter between 50-800 nm. In another embodiment, the nanoparticles have an average diameter of about 250-400 nm, or 300-350 nm, and the particle size distribution is that at least 80%, or 85%, or 90% of the nanoparticles have a diameter between 100-600 nm.

Nanoparticles of the present invention entraps amoxicillin efficiently. The loading yield, which is defined as weight of amoxicillin/total weight of the nanoparticles, is in general at least 5%, preferably at least 10%, 15%, or 20%. For example, the entrapped amoxicillin is 5-35% or 5-25% (w/w) of the total weight nanoparticles. The high loading yield of the nanoparticles are advantageous because dosing frequency can be reduced.

The nanoparticles of the present invention are able to penetrate throughout the sub-mucosal layers of the GI tract and be retained at the mucosal layer, which increases the retention time of amoxicillin for over 24 hours.

Process for Preparing the Nanoparticle Composition

The process to produce the amoxicillin nanoparticles combines polymer cross-linking with a reverse phase emulsification. The process is optimized so only the nanometer-size particles are produced with high drug loading efficiency and yield.

In the first embodiment, the process comprises the steps of: (a) mixing chitosan lactate and amoxicillin in an aqueous solution until chitosan lactate and amoxicillin are solubilized; (b) adding the mixture of (a) to an oil and dioctyl sodium sulfosuccinate and mixing to form a water-in-oil emulsion, wherein dioctyl sodium sulfosuccinate is in an amount of 1-15% (w/v) in the emulsion; (c) adding glutaraldehyde or bis[sulfosuccinimidyl] suberate to the emulsion of (b) to a final concentration of 1-15% (w/v) of glutaradehyde, (d) sonicating the mixture of (c) for a sufficient time to form small water droplets of an average diameter less than 5 µm, and to form nanoparticles within the water droplets, whereby the nanoparticles comprises chitosan crosslinked by dioctyl sodium sulfosuccinate and glutaraldehyde or by dioctyl sodium sulfosuccinate and bis[sulfosuccinimidyl] suberate, and the nanoparticles have an average diameter of 100-600 nm and have amoxicillin entrapped by the cross-linked chitosan.

In step (a), chitosan or chitosan salt and amoxicillin is mixed to dissolve in an aqueous solution. Water is a preferred aqueous solution; however, a small amount of salt or buffer can be added to water. If chitosan used is not fully dissolved in water, a small amount of acetic acid can be added to increase the solubility of chitosan. A preferred starting material is chitosan lactate, which has a smaller molecular weight (4,000-6,000 Dalton) than chitosan, and is water soluble. In general, the weight ratio of amoxicillin to chitosan is about 0.01-0.5 to 1. For example, the concentration of amoxicillin is 0.1-5 mg/mL, and the concentration of chitosan is 5-20 mg/mL.

In step (b), the chitosan solution of (a) is added to dioctyl sodium sulfosuccinate (DOSS) and an oil. The chitosan solution is immiscible with oil and DOSS helps the dispersing of the aqueous chitosan solution in oil. Any suitable oil that can form a reverse phase emulsion can be used. Suitable oils include mineral oil, vegetable oil, olive oil, salad oil, and corn oil. In one embodiment, the amount of the oil is at least 35% or 40% v/v. For example, the amount of oil is 35-60%, 40-70%, 50-80%, 60-80%, 70-90, or 75-90% v/v in the emulsion. DOSS acts bi-functionally in this reaction. In one function, DOSS is an anionic surfactant which helps to disperse the chitosan solution into oil to form water-in-oil emulsion. In another function, DOSS acts as a crosslinker to crosslink the chitosan molecules; the two carboxylate groups on the DOSS and the amino groups on the chitosan form amide bonds. The amount of dioctyl sodium sulfosuccinate used is about 1-15%, or 2-10%, or 3-8% (w/v).

In step (c), a second crosslinking agent is added. Examples of suitable crosslinking agents for this invention include homobifunctional crosslinkers such as glutaraldehyde and BS3 crosslinker (bis[sulfosuccinimidyl] suberate). Glutamic acid, which has an additional amino functional group in addition to the carboxylic groups, is not used in this invention.

In step (d), the mixture of (c) is sonicated for a sufficient time to form small water droplets in oil and to form nanoparticles within the water droplets. The sonication can be carried out in an ultrasonic bath or by an ultrasonic probe. The sonication can also be replaced by a high power mechanic force such as high-shear mixing or high-pressure homogenization, to form small water droplets in oil. During sonication, a small droplets of water-in-oil emulsion is formed and the reaction of crosslinking chitosan and entrapping amoxicillin is on-going. Typically, sonication is about 15-60 minutes or 20-40 minutes. In general the average size of the water droplets is less than 10 µm and preferably less than 5 µm. In general, 1-15%, or 2-10%, or 3-8% (w/v) of a second crosslinking agent can be used. For example, about 5% of glutaraldehyde can be used in the crosslinking reaction.

After sonication for a sufficient time, the crosslinking reaction is completed, and the crosslinked chitosan containing entrapped amoxicillin forms nanometer-sized particles. The nanoparticles can be separated from the suspension by centrifuging and collecting the pellets. The separated nanoparticles are optionally washed with a proper organic solvent such as hexane, petroleum ether, pentane, and ethanol. The nanoparticles are then dried and stored for usage.

In a second embodiment, the comprises the steps of: (a) mixing chitosan lactate and amoxicillin in an aqueous solution until chitosan lactate and amoxicillin are solubilized; (b) adding the mixture of (a) to dioctyl sodium sulfosuccinate, glutaraldehyde, and an oil and mixing to form a water-in-oil emulsion, wherein dioctyl sodium sulfosuccinate and glutaraldehyde are each in an amount of 1-15% (w/v) in the emulsion; (c) sonicating the mixture of (b) to form small water droplets of an average diameter less than 5 µm, and to form nanoparticles within the water droplets, whereby the nanoparticles comprises chitosan crosslinked by dioctyl sodium sulfosuccinate and glutaraldehyde or by dioctyl sodium sulfosuccinate and bis[sulfosuccinimidyl] suberate, and the nanoparticles have an average diameter of 100-600 nm and have amoxicillin entrapped by the crosslinked chitosan. The differences between the first and the second embodiments are only in the sequence of mixing the solution of chitosan lactate and amoxicillin with dioctyl sodium sulfosuccinate, an oil, and glutaraldehyde. All other parameters and conditions are similar.

Pharmaceutical Compositions

The present invention provides pharmaceutical compositions comprising amoxicillin nanoparticles and optionally one or more pharmaceutically acceptable carriers. The nanoparticles in the pharmaceutical compositions in general are about 1-90%, preferably 20-90%, or 30-80% for a tablet or powder formulation. The nanoparticles in the pharmaceutical compositions in general are 1-100%, preferably 20-100%, 50-100%, or 70-100% for a capsule formulation. The nanoparticles in the pharmaceutical compositions are general is 1-50%, 5-50%, or 10-40% for a liquid suspension formulation.

In one embodiment, the pharmaceutical composition can be in a dosage form such as tablets, capsules, granules, fine granules, powders, suspension, or the like. The above pharmaceutical composition can be prepared by conventional methods.

Pharmaceutically acceptable carriers, which are inactive ingredients, can be selected by those skilled in the art using conventional criteria. The pharmaceutically acceptable carriers may contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and polyvinylpyrrolidone (PVP, povidone); cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound may contain other excipients that have no bioactivity and no reaction with the active compound. Excipients of a tablet or a capsule may include fillers, binders, lubricants and glidants, disintegrators, wetting agents, and release rate modifiers. Examples of excipients of a tablet or a capsule include, but are not limited to, carboxymethylcellulose, cellulose, ethylcellulose, hydroxypropylmethylcellulose, methylcellulose, karaya gum, starch, tragacanth gum, gelatin, magnesium stearate, titanium dioxide , poly(acrylic acid), and polyvinylpyrrolidone. For example, a tablet formulation may contain inactive ingredients such as colloidal silicon dioxide, crospovidone, hypromellose, magnesium stearate, microcrystalline cellulose, polyethylene glycol, sodium starch glycolate, and titanium dioxide. A capsule formulation may contain inactive ingredients such as gelatin, magnesium stearate, and titanium dioxide. A powder oral formulation may contain inactive ingredients such as silica gel, sodium benzoate, sodium citrate, sucrose, and xanthan gum.

Method of Use

The present invention is directed to a method for treating bacterial infection such as *Helicobacter pylori* infection, *E. coli* infection, salmonella infection, ear infections, urinary tract infections such as bladder infection and gonorrhea, skin infections (infected bite wounds), dental infections, upper respiratory infection such as pneumonia, actinomycosis, malignant edema, gas gangrene, erysipelas, hemorrhagic septicemia, staphylococcosis, coryza, pasteurelosis, hemophilus influenza, Colibacillosis, and general purulent conditions caused by gram positive or negative bacterial infection; whereby the bacteria are killed and growth prevented. The present invention is also directed to a method for treating gastric or duodenal ulcers associated with *Helicobacter pylori* infection; whereby the symptoms of the disease are reduced or eliminated. The present invention further is directed to a method for eradicating *Helicobacter pylori*. The method comprises the steps of selecting a subject in need thereof, and administering the amoxicillin nanoparticle composition to the subject. A preferred route of administration is oral administration.

The present invention is useful in human medicine and in veterinary medicine. The present invention is useful in treating humans and non-human animals. For example, the present invention is useful in treating a mammal subject, such as humans, horses, pigs, cats, and dogs. The present invention is also useful in treating poultry such as chickens, ducks, and turkeys.

Dosing of the nanoparticle composition is based on the known dosage of amoxicillin for treating a particular disease and the subject condition. For example, for treating bacterial infection in an adult human, nanoparticles containing 250 to 500 mg of amoxicillin may be orally administered 3 times a day for 7 to 21 days; alternatively, nanoparticles containing 500 to 875 mg of amoxicillin may be orally administered twice a day. For treating bacterial infection in a dog or a cat, nanoparticles containing 5-10 mg amoxicillin/pound animal are administered every 12-24 hours.

The following examples further illustrate the present invention. These examples are intended merely to be illustrative of the present invention and are not to be construed as being limiting.

EXAMPLES

Example 1

Preparing Amoxicillin Nanoparticles

Chitosan lactate (10 mg, from Sigma-Aldrich), together with amoxicillin (3 mg, from Sigma-Aldrich) were dissolved in water (1 mL) at room temperature. The solution was added with moderate stirring to dioctyl sodium sulfosuccinate (DOSS) and mineral oil or vegetable oil, where the final concentration of DOSS is 5% w/v, and the final concentration of the oil is >75% v/v. Chitosan solution is immiscible with oil and DOSS plays a role in stabilizing the chitosan nanoparticles and crosslinking the chitosan molecules. Then glutaraldehyde (from Alfa-Aesar) was added to the mixture to a final concentration of 5% w/v, followed by immediate sonicating for 30 min to form an water-in-oil emulsion (small water droplets in oil). During the emulsification, cross-linking occurred and nanoparticles formed within small water droplets. Once the reaction stopped, the particles were separated from the suspension by centrifugation (200×g) for 1-5 minutes; the pellets were collected and subsequently washed with hexane. The nanoparticles were then dried for further analysis or uses.

Example 2

Nanoparticle Characterization

The nanoparticles of Example 1 were re-suspended in water with a concentration of 1 mg/mL. The size and size distribution of the particles were measured by dynamic light scattering (DLS) using the Malvern Zetasizer (ZEN 3600). To further characterize the morphology, a drop of nanoparticle suspension was placed on a silica wafer and then air-dried overnight. The wafer with dried sample on them was then coated with chromium and imaged by scanning electron microscopy (SEM).

Figure 2:
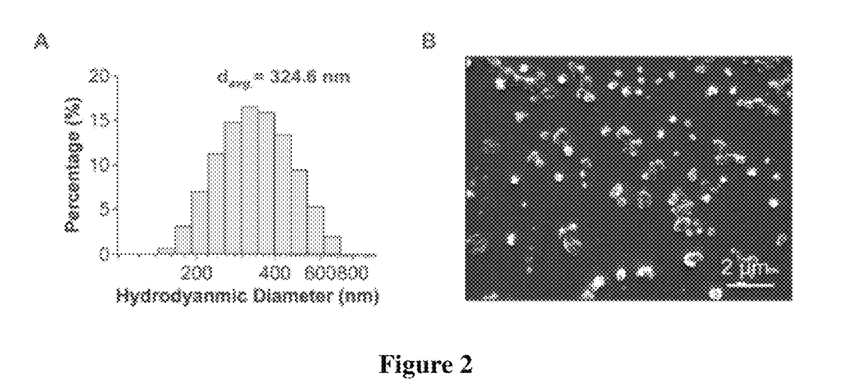

As demonstrated in FIG. 2, the particles have an average hydrodynamic diameter of 324.6 nm and a polydispersity index (PDI) of 0.2 (FIG. 2A). Under the SEM, the dry powder shows a particulate morphology with an average diameter of ~300 nm, which is consistent with the DLS measurement (FIG. 2B).

Example 3

Determining Amoxicillin Loading Yield

To measure the drug loading yield (drug weight/total weight of nanoparticles), amoxicillin-loaded nanoparticles were formulated following the same procedure described in Example 1 but with different initial drug amounts of 0.1, 1, 2.5, or 5 mg. 1 mg of dried nanoparticles was suspended with 15 mL water. The suspension was stirred vigorously at 4° C. for 12 hours to completely release the loaded drug. Then the suspension was filtered by an Amicon filter tube with a 10 kDa molecular weight cut-off. The amoxicillin concentration in the filtrate was measured and the drug loading yield was calculated.

Figure 3:
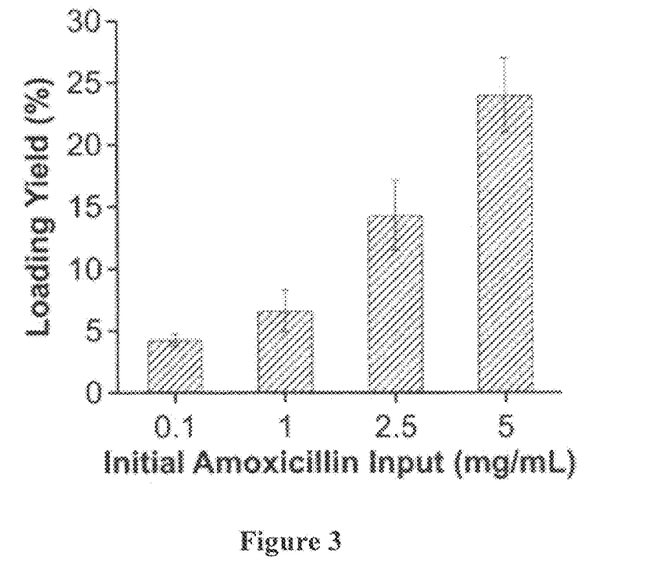

As shown in FIG. 3, the amoxicillin loading yield in the nanoparticles increases with the increase of amoxicillin initial concentration. When the amoxicillin input concentrations were 0.1, 1, 2.5 and 5 mg/mL, the corresponding loading yields were determined to be 3.9%, 6.9%, 14.2% and 24.1%, respectively. When the amoxicillin input concentrations was 3 mg/mL (Example 1), the loading yield was 20%.

Example 4

Measure In Vitro Amoxicillin Release Kinetics at Different pH

Amoxicillin-loaded nanoparticles with a drug loading yield of 20% (prepared according to Example 1) were used in this experiment.

Dried nanoparticles (total weight 5 mg, 20% loading yield) containi ng 1 mg amoxicillin were reconstituted with 50 mL 10 mM Tris-HCl buffer at pH=2.0, 5.0, 6.0 and 7.4, respectively. The suspensions were kept at 4° C. with vigorous stirring. At each time point, 0.2 mL suspension was taken and filtered by Amicon filters with 100 kDa molecular weight cut-off to collect the released drugs. The amoxicillin concentration in the filtrate was determined by HPLC. The accumulative release of amoxicillin at the time point of 24 hours was used as 100% release.

Figure 4:
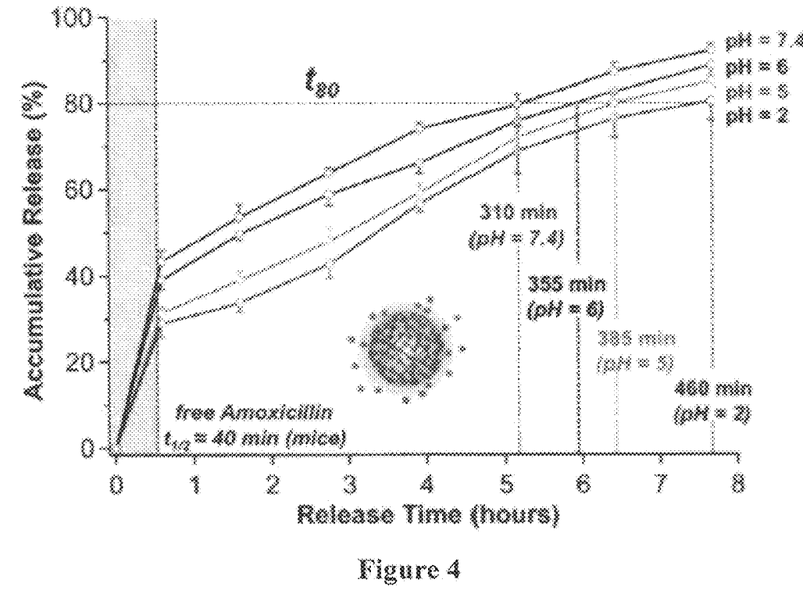

Amoxicillin release from nanoparticle formulation shows similar profiles at different pH levels (FIG. 4). A slight increase of release rate was observed with the increase of pH from 2.0 to 7.4. From the release profile, $t_{80}$ (time to release 80% of the encapsulated amoxicillin) of the nanoparticle formulations were determined as 460 (pH=2.0), 385 (pH=5.0), 355 (pH=6.0), and 310 (pH=7.4) minutes. The plasma half-life of amoxicillin in mice is reported to be about 40 minutes.

Example 5

Evaluation of In Vivo Pharmacokinetic

Figure 5:
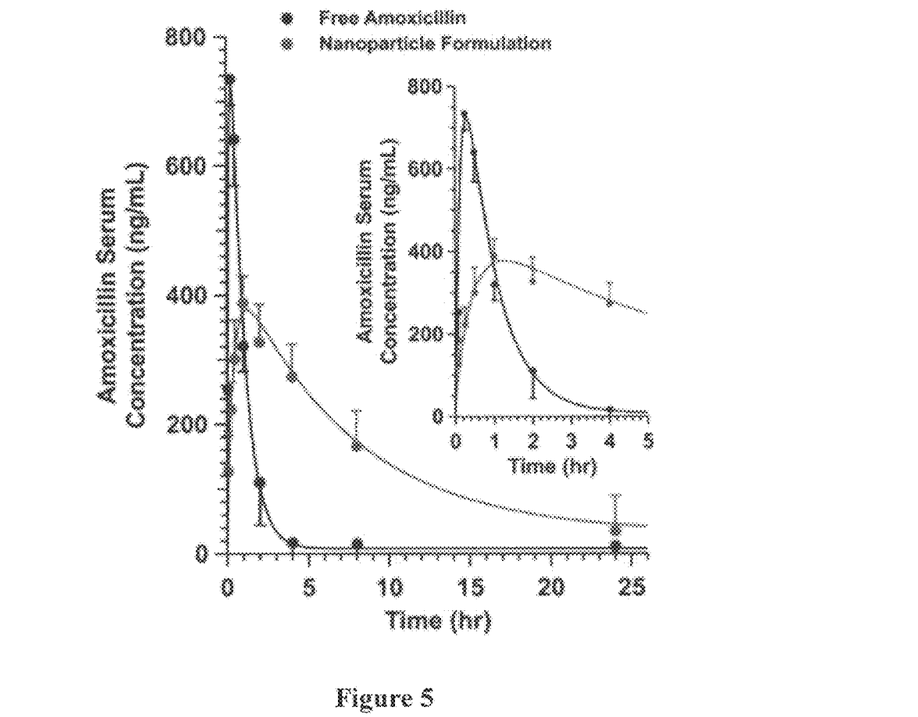

The experiments were performed on male and female ICR mice (6-8 weeks) to evaluate the amoxicillin concentration in serum. Approximately 0.3 mL nanoparticle suspension containing 10 mg nanoparticles with a drug loading yield of 20% (Example 1) was orally administered to each mouse. Following the gavage, 50 μL of blood were collected at 5 min, 15 min, 30 min, 1 hr, 2 hr, 4 hr, 8 hr and 24 hr from each mouse. The same dose of free amoxicillin (2 mg) was also tested in parallel as a control. Each testing group contained 10 mice (five male and five female). The concentration of amoxicillin in each collected serum sample was determined by HPLC. The results are shown in FIG. 5.

When free amoxicillin was administered, the serum concentration of amoxicillin peaked at 15 minutes, and then dropped to below 50% of the peak value after 1 hour and below 20% after 2 hours. In contrast, when the nanoparticle formulation was administered, the serum concentration of amoxicillin peaked at 1 hour, and remained above 50% of the peak concentration after 8 hours. This significant extension of systemic drug concentration will increase the therapeutic duration of amoxicillin. Based on these results, it is expected that the nanoparticle formulation of amoxicillin will have at least 5~10 folds increase of therapeutic duration when comparing with free amoxicillin. The area under the curve represents the total measured amount of drug in the circulation. Notably, free amoxicillin showed a smaller area when compared with that of the nanoparticle formulation, which is likely due to drug clearance in the stomach and through the systemic renal clearance.

Example 6

In Vitro MIC (Minimal Inhibitory Concentration) and MBC (Minimal Bactericidal Concentration)

Bacterial culture. In the study, E. coli bacteria were first cultured on agar plates. Fresh colonies were then transferred to LB medium and incubated overnight at 37° C. under moderate reciprocal shaking. H. pylori SS1 strain was maintained on Columbia agar supplemented with 5% laked horse blood (Thermo Scientific) at 37° C. under microaerobic conditions (10% CO2, 85% N2, and 5% O2). Broth cultures of H. pylori were prepared by subculturing fresh colonies from agar plates into brain heart infusion (BHI) containing 5% fetal bovine serum and incubated overnight at 37° C. under microaerobic conditions with moderate reciprocal shaking.

In vitro MIC test of the nanoparticle formulation. Overnight broth cultures of H. pylori SS1 or E. coli were centrifuged at 5000×g for 10 min to obtain a bacterial pellet. The pellet was adjusted to an optical density at 600 nm (OD600) of 1.0, corresponding to approximately $1\times10^8$ colony-forming units (CFU)/mL. Amoxicillin-loaded nanoparticle suspension (same preparation as Example 5) was diluted to various concentrations with an added volume of culture medium in a 96 well plate and then bacteria with a concentration of $1\times10^7$ CFU/mL was added. Samples were placed under culturing conditions and incubated at 37° C. The OD 600 absorption was measured over a 72-hour time span by microplate reader. Free amoxicillin was tested in parallel as a control.

In vitro MBC test of the nanoparticle formulation. Overnight broth cultures of H. pylori SS1 or E. coli were centrifuged at 5000×g for 10 min to obtain a bacterial pellet. The pellet was adjusted to an optical density at 600 nm (OD600) of 1.0, corresponding to approximately $1\times10^8$ colony-forming units (CFU)/mL. Then 10 μL/well of bacterial suspension containing $1\times10^6$ CFU bacteria was added to a 96-well plate containing 190 μL of BHI medium supplemented with 5% FBS along with various concentrations of amoxicillin-loaded nanoparticles. The plate was incubated at 37° C. under microaerobic conditions on a reciprocal shaker. After incubation for 30 min, a series of 10-fold dilutions of the bacterial suspension (1:10 to $1:10^5$) were prepared, and 5 μL from each diluted sample was inoculated onto a Columbia agar plate with proper supplement. The plates were cultured in the incubator for 4 days before counting colonies. Free amoxicillin was tested in parallel as a control (see FIGS. 6A and 6B).

Results

Figure 6:
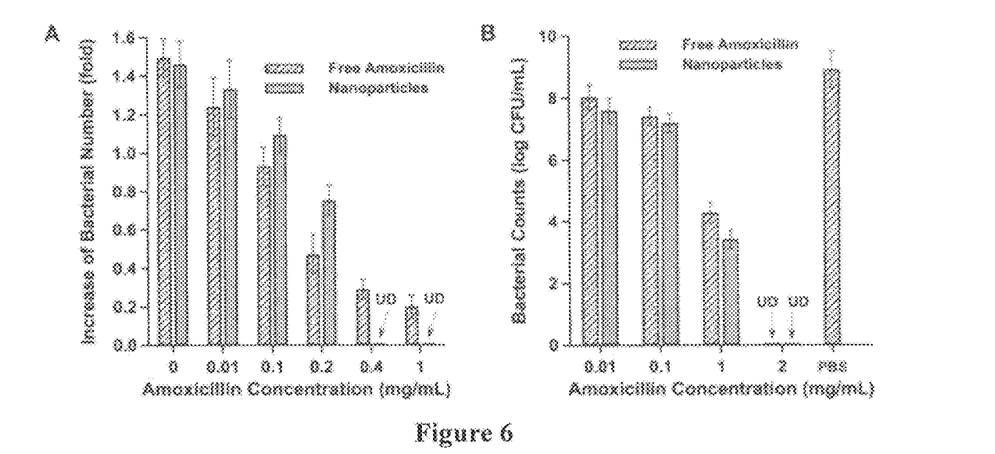

Nanoparticle formulation showed similar antibacterial activity against H. pylori when compared to free amoxicillin (FIG. 6). The MIC study shows that the bacterial growth was completely inhibited at amoxicillin concentration of 0.4 mg/mL of the nanoparticle formulation (FIG. 6A). In the MBC study, eradication of H. pylori bacteria was observed when the amoxicillin concentration reached 2 mg/mL (FIG. 6B)

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. Nanoparticles comprising crosslinked chitosan and amoxicillin, wherein amoxicillin is entrapped by the crosslinked chitosan, and the nanoparticles have an average diameter of about 250-400 nm, wherein the chitosan is crosslinked by glutaraldehyde or bis[sulfosuccinimidyl] suberate, the nanoparticles comprise less than 2% (w/w) of any other polymer that is not chitosan, and comprises at least 5% (w/w) of amoxicillin, wherein the nanoparticles are prepared by a process comprising the following steps:
(a) mixing chitosan or chitosan lactate and amoxicillin in an aqueous solution until chitosan or chitosan lactate and amoxicillin are solubilized;
(b) adding the aqueous solution of (a) to an oil and dioctyl sodium sulfosuccinate and mixing to form a water-in-oil emulsion, wherein dioctyl sodium sulfosuccinate is in an amount of 1-15% (w/v) in the emulsion;
(c) adding glutaraldehyde or bis[sulfosuccinimidyl] suberate to the emulsion of (b) to a final concentration of 1-15% (w/v) of glutaradehyde,
(d) sonicating the mixture of (c) to form water droplets in oil, and to form nanoparticles within the water droplets, and
(e) separating and collecting the nanoparticles.

2. The nanoparticles of claim 1, wherein the nanoparticles have an average diameter of about 300-350 nm.

3. The nanoparticles of claim 1, wherein the size distribution the nanoparticles is that at least 80% of the nanoparticles have a diameter between 50-800 nm.

4. The nanoparticles of claim 3, wherein the size distribution the nanoparticles is that at least 80% of the nanoparticles have a diameter between 100-600 nm.

5. The nanoparticles of claim 1, wherein the chitosan is crosslinked by glutaraldehyde.

6. The nanoparticles of claim 1, wherein the weight of the entrapped amoxicillin is at least 10% of the total weight of the nanoparticles.

7. The nanoparticle composition of claim 1, which contains less than 1% (w/w) of any other polymer that is not chitosan.

8. A pharmaceutical composition comprising the nanoparticles of claim 1 and a pharmaceutical acceptable carrier, wherein the composition is in an oral form of a capsule, a tablet, powder, or a suspension.

9. The pharmaceutical composition of claim 8, in a form of powder or a tablet.

10. A method of treating bacterial infection, comprising the step of:
orally administering to a subject suffering from bacterial infection the nanoparticles of claim 1, in an amount effective to treat bacterial infection.

11. The method of claim 10, wherein the bacterial infection is selected from the group consisting of *Helicobacter pylori* infection, *E. coli* infection, *salmonella* infection, ear infection, urinary tract infection, skin infection, dental infection, actinomycosis, malignant edema, gas gangrene, erysipelas, pneumonia, hemorrhagic septicemia, staphylococcosis, coryza, pasteurelosis, hemophilus influenza, Colibacillosis, and general purulent conditions caused by gram positive or negative bacterial infection, whereby the bacteria are killed and growth prevented.

12. The method of claim 11, which treats gastric or duodenal ulcers associated with *Helicobacter pylori* infection; whereby the symptoms of the disease is reduced or eliminated.

\* \* \* \* \*